(12) United States Patent
Onuma et al.

(10) Patent No.: US 10,281,449 B2
(45) Date of Patent: *May 7, 2019

(54) STATE DETERMINATION METHOD AND STATE DETERMINATION DEVICE

(71) Applicant: NABTESCO CORPORATION, Tokyo (JP)

(72) Inventors: Yoshinori Onuma, Tokyo (JP); Takuya Shirata, Tokyo (JP); Yasuhito Ida, Tokyo (JP)

(73) Assignee: NABTESCO CORPORATION, Tokyo (JP)

( * ) Notice: Subject to any disclaimer, the term of this patent is extended or adjusted under 35 U.S.C. 154(b) by 400 days.

This patent is subject to a terminal disclaimer.

(21) Appl. No.: 14/392,335

(22) PCT Filed: Jul. 1, 2014

(86) PCT No.: PCT/JP2014/067546
§ 371 (c)(1),
(2) Date: Dec. 28, 2015

(87) PCT Pub. No.: WO2015/002196
PCT Pub. Date: Jan. 8, 2015

(65) Prior Publication Data
US 2016/0161463 A1    Jun. 9, 2016

(30) Foreign Application Priority Data

Jul. 2, 2013 (JP) .................... 2013-138837

(51) Int. Cl.
*G01N 33/28* (2006.01)
*G01N 21/25* (2006.01)
(Continued)

(52) U.S. Cl.
CPC ....... *G01N 33/2888* (2013.01); *G01N 21/251* (2013.01); *G01N 21/27* (2013.01);
(Continued)

(58) Field of Classification Search
CPC .................................................. G01N 33/2888
(Continued)

(56) References Cited

U.S. PATENT DOCUMENTS

| 5,504,573 A * | 4/1996 | Cheiky-Zelina ... G01N 15/0266 |
| | | 250/301 |
| 9,201,055 B2 * | 12/2015 | Ohnuma ............. G01N 21/251 |
| 9,435,731 B2 * | 9/2016 | Ohnuma ............. G01N 21/251 |

FOREIGN PATENT DOCUMENTS

| EP | 2 447 704 A1 | 5/2012 |
| JP | 5-273121 A | 10/1993 |

(Continued)

OTHER PUBLICATIONS

Extended European Search Report as issued in European Patent Application No. 14820030.6, dated Dec. 2, 2016.
(Continued)

*Primary Examiner* — Hina F Ayub
*Assistant Examiner* — Amanda Merlino
(74) *Attorney, Agent, or Firm* — Pillsbury Winthrop Shaw Pittman, LLP

(57) ABSTRACT

In a method of determining a deterioration state of an object, the deterioration state of the object is determined by determining whether a calculated value reaches a state determination threshold value or not, the calculated value utilizing at least one of brightness and a color component value calculated from a detection value detected by an optical sensor. The optical sensor includes an examination section containing liquid, a light emitting element emitting detection light toward the examination section, and a light receiving (Continued)

element detecting color information of the detection light traveled through the liquid.

8 Claims, 12 Drawing Sheets

(51) Int. Cl.
*G01N 21/27* (2006.01)
*G01N 21/85* (2006.01)

(52) U.S. Cl.
CPC ... *G01N 21/8507* (2013.01); *G01N 2201/062* (2013.01); *G01N 2201/12* (2013.01)

(58) Field of Classification Search
USPC .......................................................... 356/70
See application file for complete search history.

(56) References Cited

FOREIGN PATENT DOCUMENTS

| JP | 6-24541 | 2/1994 |
|---|---|---|
| JP | 11-235097 A | 8/1999 |
| JP | 2000-146696 A | 5/2000 |
| JP | 2006-177715 A | 7/2006 |
| JP | 2010-145107 A | 7/2010 |
| JP | 2012-143837 A | 8/2012 |

OTHER PUBLICATIONS

Ossia, C.V., et al,, "Novel Chromatic Technique Based on Optical Absorbance in Characterizing Mineral Hydraulic Oil Degradation," Advances in Tribology, vol. 49, No. 200305, Jan. 2012, 1SSN:1687-6915, XP055270321, 9 pages.

Yamaguchi, T., et al., "Investigation of Oil Contamination by Colorimetric Analysis ©," Lubrication Engineering, Oct. 2001, XP055136991, pp. 12-17.

International Search Report as issued in International Patent Application No. PCT/JP2014/067546, dated Sep. 2, 2014.

International Preliminary Report on Patentability and the Written Opinion of the International Searching Authority as issued in International Patent Application No. PCT/JP2014/067546, dated Jan. 5, 2016.

\* cited by examiner

STATE DETERMINATION METHOD AND STATE DETERMINATION DEVICE

CROSS-REFERENCE TO RELATED APPLICATIONS

This application is the U.S. National Stage of PCT/JP2014/067546, filed Jul. 1, 2014, which in turn claims priority to Japanese Patent Application No. JP 2013-138837, filed Jul. 2, 2013. The contents of these applications are incorporated herein by reference in their entireties.

TECHNICAL FIELD

The present invention relates to a state determination method and a state determination device.

BACKGROUND

There has been known a deterioration monitor device for oil such as lubricant using an optical sensor. The monitor detects a red-green-blue (RGB) absorbance in visible light that travels through oil and then estimates a deterioration degree of the oil from the detected RGB absorbance (see, for example, Patent Literature 1).

The oil deterioration monitor device described in Patent Literature 1 detects the absorbance as a voltage value. The light absorbance of the oil generally decreases as time proceeds. Patent Literature 1 disclosed the voltage values over time for various types of oils, and the oil deterioration monitor device continuously obtains changes in the voltage value to monitor the deterioration of the lubricant continuously and sensitively.

RELEVANT REFERENCES

List of Relevant Patent Literature

Patent Literature 1: Japanese Patent Application Publication No. Hei 6-34541

SUMMARY

Meanwhile, the oil deterioration monitor device described in Patent Literature 1 tries to monitor the deterioration of the lubricant continuously and with a high sensitivity. Patent Literature 1 does not mention in what situation the device determines liquid such as oil as deteriorated. Therefore there is a need for a state determination method and a state determination device with which the deterioration state of the liquid such as oil can be easily determined.

Moreover, for machines using oil such as lubricant, it would be advantageous to determine deterioration states of the machines by utilizing a fact that the oil includes impurity substances when the machines are broken. Therefore there is a need for a state determination method and a state determination device with which a deterioration state(s) of objects including liquid such as oil and/or the machines can be easily determined.

An object of the invention is to provide a state determination method and a state determination device with which a deterioration state of an object can be easily determined.

Means and its effects for achieving the object will be now described. In a method of determining a deterioration state of an object for solving the above-mentioned problem, the deterioration state of the object is determined by determining whether a calculated value reaches a state determination threshold value, the calculated value utilizing at least one of brightness and a color component value calculated from a detection value detected by an optical sensor.

In the state determination method, preferably utilized is a fact that the brightness, a maximum color component value, and a minimum color component value calculated from the detection value detected by the optical sensor change depending on operating time of the object.

According to the method, the deterioration state of the object is determined by determining whether a calculated value reaches a state determination threshold value or not. The calculated value utilizes at least one of brightness and a color component value calculated from a detection value detected by an optical sensor. In this way, the state of the object can be easily determined from the comparison between the calculated value and the state determination threshold value.

In the state determination method, it is preferable that the calculated value include the brightness that decreases as the operating time increases, and when the calculated brightness is less than or equal to the state determination threshold value, it is determined that the object is in a deteriorated state.

According to the method, when the calculated brightness is less than or equal to the state determination threshold value, it is determined that the object is in a deteriorated state. When the liquid is contaminated with impurity substances generated from a machine using the liquid, the brightness of the liquid significantly changes. Therefore when the object is deteriorated, the deterioration can be easily determined.

In the above-mentioned state determination method, the calculated value may include a maximum color difference, which is a difference between the maximum color component value and the minimum color component value. The maximum color difference increases as the operating time increases and then decreases once it reaches an extreme value. When the calculated maximum color difference reaches the extreme value and is less than or equal to the state determination threshold value, it may be determined that the object is in a deteriorated state.

According to the method, when the calculated maximum color difference reaches the extreme value and is less than or equal to the state determination threshold value, it is determined that the object is in a deteriorated state. In case of a highly-transparent liquid whose color tends to be easily changed due to oxidation, deterioration and the like, the maximum color difference significantly changes. Therefore when the object is deteriorated, the deterioration can be easily determined.

In the above-mentioned state determination method, the calculated value may include a maximum color ratio, which is a ratio of the maximum color component value to the minimum color component value, the maximum color ratio increases as the operating time increases. When the calculated maximum color ratio is larger than or equal to the state determination threshold value, it may be determined that the object is in a deteriorated state.

According to the method, when the calculated maximum color ratio is larger than or equal to the state determination threshold value, it is determined that the object is in a deteriorated state. In case of a highly-transparent liquid whose color tends to be easily changed due to oxidation, deterioration and the like, the maximum color ratio significantly changes. Therefore when the object is deteriorated, the deterioration can be easily determined.

In the above-mentioned state determination method, the calculated value may include the brightness that decreases as the operating time increases; a maximum color difference, which is a difference between the maximum color component value and the minimum color component value, wherein the maximum color difference increases as the operating time increases and then decreases once it reaches an extreme value; and an integral of the maximum color difference, which is an integrated value obtained by adding the maximum color difference each time the brightness changes as the operating time passes. When the calculated integral of the maximum color difference is larger than or equal to the state determination threshold value, it may be determined that the object is in a deteriorated state.

According to the method, when the calculated integral of the maximum color difference is larger than or equal to the state determination threshold value, it is determined that the object is in a deteriorated state. Therefore, comparing with the case where the deterioration state of the object is determined based on the relation between the brightness and the maximum color difference, this embodiment can easily determine the state since it requires only one parameter, i.e. the integral of the maximum color difference.

In the above-mentioned state determination method, the calculated value may include the brightness that decreases as the operating time increases; a maximum color ratio, which is a ratio of the maximum color component value to the minimum color component value, wherein the maximum color ratio increases as the operating time increases; and an integral of the maximum color ratio, which is an integrated value obtained by adding the maximum color ratio each time the brightness changes as the operating time passes. When the calculated integral of the maximum color ratio is larger than or equal to the state determination threshold value, it may be determined that the object is in a deteriorated state.

According to the method, when the calculated integral of the maximum color ratio is larger than or equal to the state determination threshold value, it is determined that the object is in a deteriorated state. Therefore, comparing with the case where the deterioration state of the object is determined based on the relation between the brightness and the maximum color difference, this embodiment can easily determine the state since it requires only one parameter, i.e. the integral of the maximum color ratio.

In the state determination method, the object may be the liquid, and the state determination threshold value may be a liquid deterioration determination threshold value to determine whether the liquid is deteriorated or not.

According to the above-described method, the state determination threshold value is a liquid deterioration determination threshold value to determine whether the liquid is deteriorated or not. Therefore it is possible to easily determine a deterioration state of the object. In the state determination method, the object may be a machine using the liquid, and the state determination threshold value may be a failure determination threshold value to determine whether the machine is broken or not.

According to the above-described method, the state determination threshold value is a failure determination threshold value to determine whether the machine is broken or not. Therefore it is possible to easily determine that the machine is broken. A state determination device for solving the above-stated problem may include a determination unit performing the above-described state determination method.

The device includes the determination unit performing the above-described state determination method. Therefore, the state of the object can be easily determined from the comparison between the calculated value and the state determination threshold value.

According to the invention, it is possible to easily determine a deterioration state of an object.

DESCRIPTION OF THE PREFERRED EMBODIMENTS

First Embodiment

A state determination method and a state determination device according to a first embodiment will be now described with reference to FIGS. 1-4. The state determination device may be provided in machines using liquid such as lubricant, hydraulic oil and the like to determine deterioration states of oil and the machines that require the oil. When a movable component that requires oil is broken, impurity substances penetrate in the oil by friction or the like (contamination). Therefore, failure of the machine can be determined from the state of the oil. In this case, an object is the oil and/or the machine.

Figure 1:
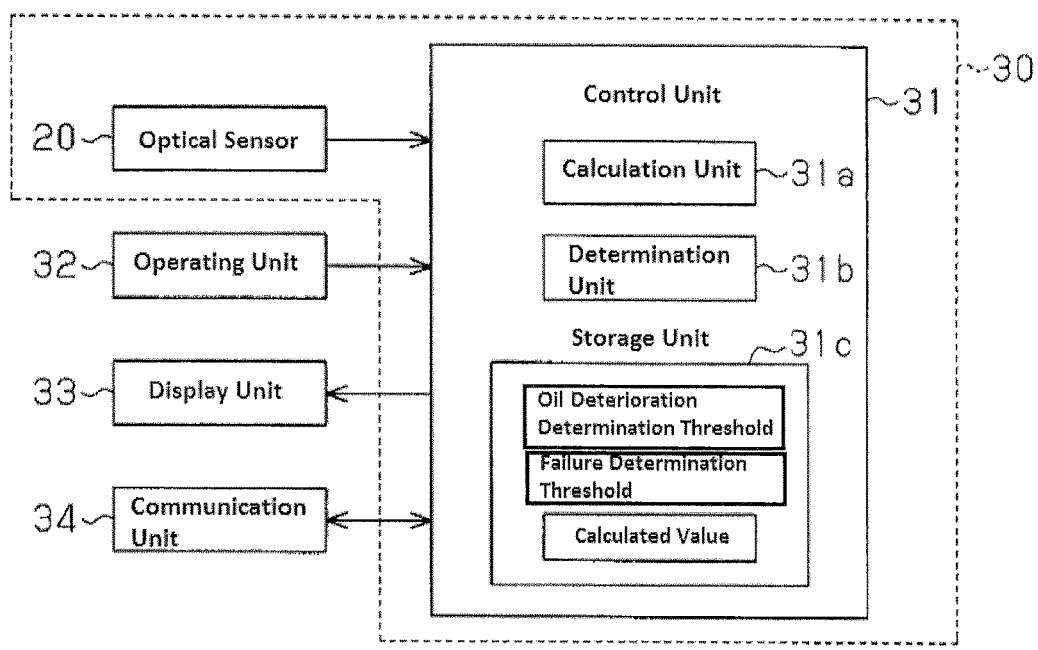
FIG. 1 is a block diagram schematically showing the structure of a state determination device.

Referring to FIG. 1, a state determination device 30 may include an optical sensor 20 and a control unit 31 that determines a deterioration state of an object and/or oil. The control unit 31 may include a calculation unit 31*a* that calculates a calculated value from a detected value which the optical sensor 20 detects, a determination unit 31*b* that determines a deterioration state of an object based on the calculated value obtained from the calculation unit 31*a*, and a storage unit 31*c* that stores a state determination threshold value and the like.

The control unit 31 may be separately provided so as to be attached to a movable component of a machine or integrally provided with a controller of the machine that includes the movable component. It is preferable that the control unit 31 be coupled to an operating unit 32 through which the control unit 31 is operated. The control unit 31 may perform a determination process or output a determination result in response to the operation of the operating unit 32. It is also preferable that the control unit 31 be coupled to a display unit 33 that displays the determination result, an operation result and the like. It is also preferable that the control unit 31 be coupled to a communication unit 34 through which the determination result, the state determination threshold value and the like are wire or wireless communicated.

The calculation unit 31a may calculate a brightness of oil. The brightness that the calculation unit 31a calculates is herein referred to as a detection brightness. The determination unit 31b may determine a deterioration state of an object by judging whether the detection brightness calculated by the calculation unit 31a reaches the state determination threshold value or not. The storage unit 31c may store a failure determination threshold value and an oil deterioration determination threshold value which may also be referred to as a liquid deterioration determination threshold value that is the state determination threshold value that the determination unit 31b uses.

Figure 2:
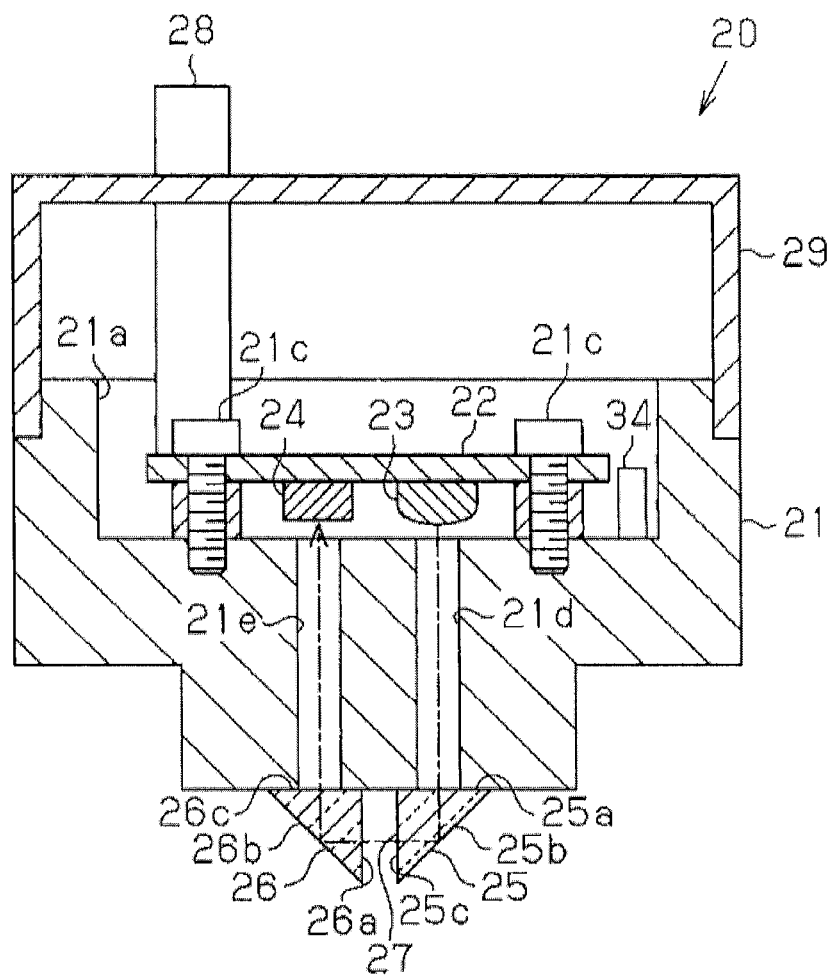
FIG. 2 is a sectional view of an optical sensor showing its structure.

The structure of the optical sensor 20 will be now described with reference to FIG. 2. The optical sensor 20 may include a column-shaped housing 21 made of metal or resin. A container section 21a may be provided in an upper area of the housing 21. The container section 21a may be covered with a cylindrical cover 29 that has a closed bottom.

The container section 21a may contain a circuit substrate 22. The circuit substrate 22 may be fixed on the housing 21 with at least one screw 21c. A communication line 28 that includes a power source line and a signal line may be coupled to the circuit substrate 22.

A light emitting element 23, a color sensor 24 which is a light receiving element, and various electronic components (not shown) may be provided on the circuit substrate 22. The light emitting element 23 is a commonly-known element that emits white detection light such as a white LED. The color sensor 24 is an RGB sensor in this embodiment and outputs R, G, B values as color information corresponding to an intensity of the detection light to the device through the communication line 28.

The housing 21 may have a first through hole 21d extending in an optical axis direction of the detection light. The first through hole 21d extends from the bottom of the container section 21a to the bottom of the housing 21. A first prism 25 may be provided on the bottom of the housing 21 at an exit of the first through hole 21d. The first prism 25 may be a right-angle prism made of a translucent material such as quartz and glass. The first prism 25 may have an incident surface 25a where the detection light traveled through the first through hole 21d enters, a reflection surface 25b where the detection light entered from the incident surface 25a is reflected, and an exit surface 25c through which the detection light reflected at the reflection surface 25b exits out.

The incident surface 25a and the exit surface 25c may be optical-polished. The reflection surface 25b may be formed of a metal deposited film and a protection film. The metal deposited film is, for example, a thin aluminum film and formed on the outer side of the translucent material. The protection film is, for example, a silicon dioxide thin film or a magnesium fluoride thin film formed on the outer side of the metal deposited film to protect the metal deposited film. An angle of the reflection surface 25b with the incident surface 25a may be set such that a light path of the light entering the reflection surface 25b is reflected at 90 degrees from the incident direction.

A second prism 26 may be provided on the bottom of the housing 21. The second prism 26 may be disposed with a gap from the first prism 25. The second prism 26 may have the same structure as the first prism 25 and have an incident surface 26a, a reflection surface 26b, and an exit surface 26c. The gap between the first prism 25 and the second prism 26 may be an oil entering gap 27 where liquid such as oil enters and stays thereon and the gap serves as an examination section.

The housing 21 may have a second through hole 21e extending in parallel with the first through hole 21d. The second through hole 21e may extend from the bottom of the container section 21a to the bottom of the housing and may be disposed between the second prism 26 and the color sensor 24.

The white detection light beam emitted from the light emitting element 23 travels straight through the first through hole 21d and enters into the first prism 25. The light path of the detection light is then bent at 90 degrees by the reflection surface 25b and enters into the oil entering gap 27 from the exit surface 25c. The detection light further penetrates the oil in the oil entering gap 27 and then enters the second prism 26. The light path of the detection light entering the second prism 26 is bent at 90 degrees by the reflection surface 26b and then travels straight through the second through hole 21e. Finally, the detection light is received by the color sensor 24. In other words, the light path of the detection light emitted from the light emitting element 23 is reversed at 180 degrees by the first prism 25 and the second prism 26. The detection light that has traveled through the oil becomes light in which a wavelength region corresponding to the hue of the oil is absorbed.

Figure 3:
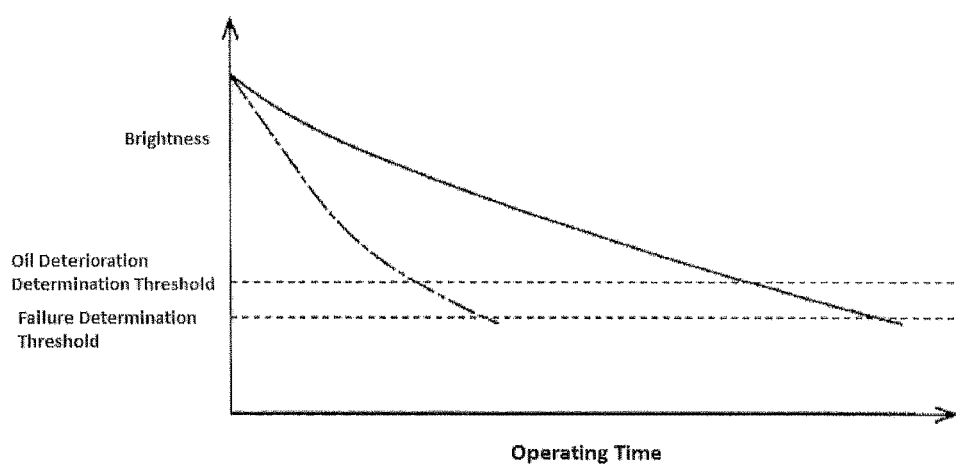
FIG. 3 illustrates a relationship between an operating time and brightness used for determining a state according to a first embodiment.

As illustrated in FIG. 3, the brightness may decrease as the operating time of the machine using oil increases. The brightness ($\Delta E$) is calculated from the formula (1) shown below of color component values, or an R value, a G value, and a B value. The dashed-dotted line in FIG. 3 shows a change in the brightness with respect to the operating time when a load on a movable component of the machine is large. The solid line in FIG. 3 shows a change in the brightness with respect to the operating time when the load on the movable component of the machine is small. Here, the operating time corresponds to an hour of use of the object.

Formula 1

$$\Delta E = \sqrt{R^2 + G^2 + B^2} \qquad (1)$$

The determination unit 31b may determine a deterioration state of the oil based on the brightness of the oil calculated from the detection value obtained from the optical sensor 20. More specifically, the determination unit 31b may determine the deterioration state of the oil based on comparison between the detection brightness of the oil calculated from the detection value obtained from the optical sensor 20 and the oil deterioration determination threshold value. The oil deterioration determination threshold value is a threshold value for determining whether the oil is deteriorated or not. When the detection brightness is less than or equal to the oil deterioration determination threshold value, the determination unit 31b determines that the oil is deteriorated.

The determination unit 31b may determine a state of the machine based on the brightness of the oil calculated from the detection value obtained from the optical sensor 20.

More specifically, the determination unit 31b may determine the state of the machine based on comparison between the detection brightness of the oil calculated from the detection value obtained from the optical sensor 20 and the failure determination threshold value. The failure determination threshold value is a threshold value for determining whether the machine is broken down or not and its value is smaller than the oil deterioration determination threshold value. When the detection brightness is less than or equal to the failure determination threshold value, the determination unit 31b determines that the machine is broken down. The failure state of the machine corresponds to the deterioration state.

How the state determination device 30 configured as described above determines a state will be now described with reference to FIG. 4. The state determination device 30 may periodically perform a state determination of the machine equipped with a movable component when a predetermined operating time has elapsed. Alternatively the state determination may be performed whenever a need arises or only when a user instructs.

Figure 4:
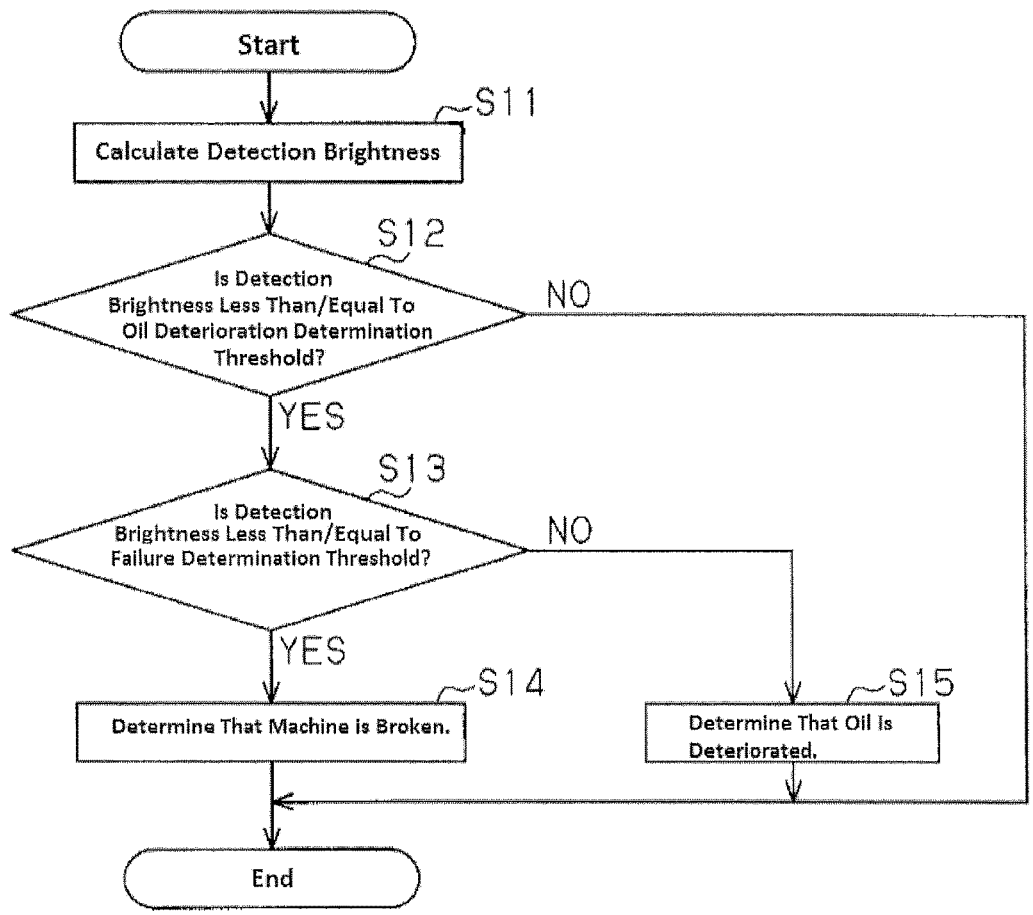
FIG. 4 is a flow chart showing a state determination method according to the first embodiment.

Referring to FIG. 4, the control unit 31 of the state determination device 30 may initiate a state determination in response to an instruction to perform the state determination. The control unit 31 calculates a detection brightness from the optical sensor 20 (step S11). More specifically, the calculation unit 31a calculates the detection brightness from a value detected by the color sensor 24 of the optical sensor 20.

The control unit 31 may subsequently determine whether the detection brightness is less than or equal to the oil deterioration determination threshold value (step S12). More specifically, when the determination unit 31b determines that the detection brightness calculated by the calculation unit 31a is larger than the oil deterioration determination threshold value (step S12: NO), the determination unit 31b determines that the oil is not deteriorated and the determination process is completed.

Whereas when the determination unit 31b determines that the detection brightness calculated by the calculation unit 31a is less than or equal to the oil deterioration determination threshold value (step S12: YES), the determination unit 31b further determines whether the detection brightness is less than or equal to the failure determination threshold value (step S13). More specifically, when the determination unit 31b determines that the detection brightness is larger than the failure determination threshold value (step S13: NO), the determination unit 31b determines that the oil is deteriorated and the determination process is completed (step S15). In other words, when the detection brightness is larger than the failure determination threshold value and less than or equal to the oil deterioration determination threshold value, the determination unit 31b determines that the oil is deteriorated but the machine is not broken.

Meanwhile, when the determination unit 31b determines that the detection brightness is smaller than or equal to the failure determination threshold value (step S13: YES), the determination unit 31b determines that the machine is broken (step S14) and the determination process is completed. In other words, the determination unit 31b determines that the oil is contaminated with impurity substances due to failure of the machine since the detection brightness is less than or equal to the failure determination threshold value, and so determination unit 31b determines that the machine is broken.

As described above, according to the embodiment, the brightness is calculated from the value detected by the optical sensor 20, and it is possible to easily determine the deterioration of the oil using the oil deterioration determination threshold value and determine the failure of the machine using the failure determination threshold value.

According to the above-described embodiment, the following advantageous effects can be obtained. (1) Deterioration state of an object such as oil and/or a machine is determined based on whether the calculated value from the detection value detected by the optical sensor 20 reaches the state determination threshold value or not. Therefore, the state of the oil and/or the machine can be easily determined from the comparison between the calculated value and the state determination threshold value.

(2) When the detection brightness is less than or equal to the failure determination threshold value, the machine is determined to be broken. When the oil is contaminated with impurity substances generated from the machine using the oil, the brightness of the oil significantly changes. This fact can be utilized to determine whether the machine is in a failure state.

Second Embodiment

A state determination method according to a second embodiment will be now described with reference to FIGS. 5-6. The state determination method according to the second embodiment is different from the first embodiment in that a maximum color difference is used as the calculated value instead of the brightness. The difference from the first embodiment will be mainly hereunder described. The state determination device 30 of the second embodiment may have the same structure as the state determination device 30 of the first embodiment shown in FIG. 1. The calculation unit 31a may store the calculated detection maximum color difference in the storage unit 31c until the oil is replaced by a new one. The determination unit 31b may determine whether the detection maximum color difference reaches an extreme value or not.

Figure 5:
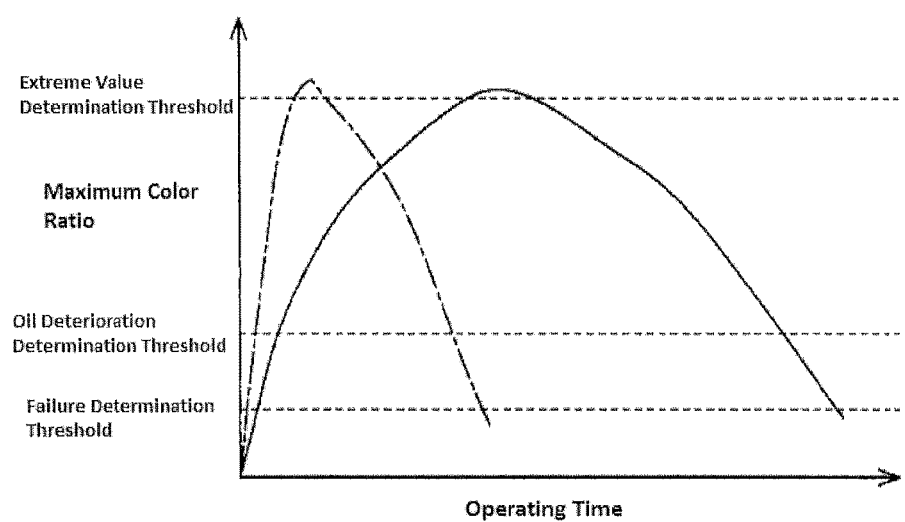
FIG. 5 illustrates a relationship between an operating time and a maximum color difference used for determining a state according to a second embodiment.

As illustrated in FIG. 5, the maximum color difference may increase as the operating time of the machine using oil increases and then decreases once the maximum color difference reaches the extreme value. The dashed-dotted line in FIG. 5 shows a change in the maximum color difference with respect to the operating time when a load on a movable component of the machine is large. The solid line in FIG. 5 shows a change in the maximum color difference with respect to the operating time when the load on the movable component of the machine is small. Here, the operating time corresponds to an hour of use of the object.

A maximum difference in color component (the maximum color difference) used for the state determination will be now described. A difference between each color (a component color difference) is an absolute value of a different between two of R, G, B, which is represented as |R−G|, |G−B|, and |R−B| respectively. The one having the largest value among these component color differences is the maximum color difference. In other words, the maximum color difference is a difference between the maximum color component value and the minimum color component value. The minimum color component value generally corresponds to the B value and the maximum color component value generally corresponds to the R value among the R, G, B values, so only the color difference |R−B| may be calculated and it may be used as the maximum color difference.

The determination unit 31b may determine a deterioration state of the oil based on the maximum color difference of the oil calculated from the detection value obtained from the optical sensor 20. More specifically, the determination unit 31*b* may determine the deterioration state of the oil based on comparison between the detection maximum color difference of the oil calculated from the detection value obtained from the optical sensor 20 and the oil deterioration determination threshold value. The oil deterioration determination threshold value is a threshold value for determining whether the oil is deteriorated or not. When the detection maximum color difference is less than or equal to the oil deterioration determination threshold value, the determination unit 31*b* determines that the oil is deteriorated.

The determination unit 31*b* may determine a state of the machine based on the maximum color difference of the oil calculated from the detection value obtained from the optical sensor 20. More specifically, the determination unit 31*b* may determine the state of the machine based on comparison between the detection maximum color difference of the oil calculated from the detection value obtained from the optical sensor 20 and the failure determination threshold value. The failure determination threshold value is a threshold value for determining whether the machine is broken down or not and its value is smaller than the oil deterioration determination threshold value. When the detection maximum color difference is less than or equal to the failure determination threshold value, the determination unit 31*b* determines that the machine is broken down. The failure state of the machine corresponds to the deterioration state.

How the state determination device 30 configured as described above determines a state will be now described with reference to FIG. 6. The state determination device 30 may periodically perform a state determination of the machine equipped with a movable component when a predetermined operating time has elapsed. Alternatively, the determination process may performed whenever a need arises.

Figure 6:
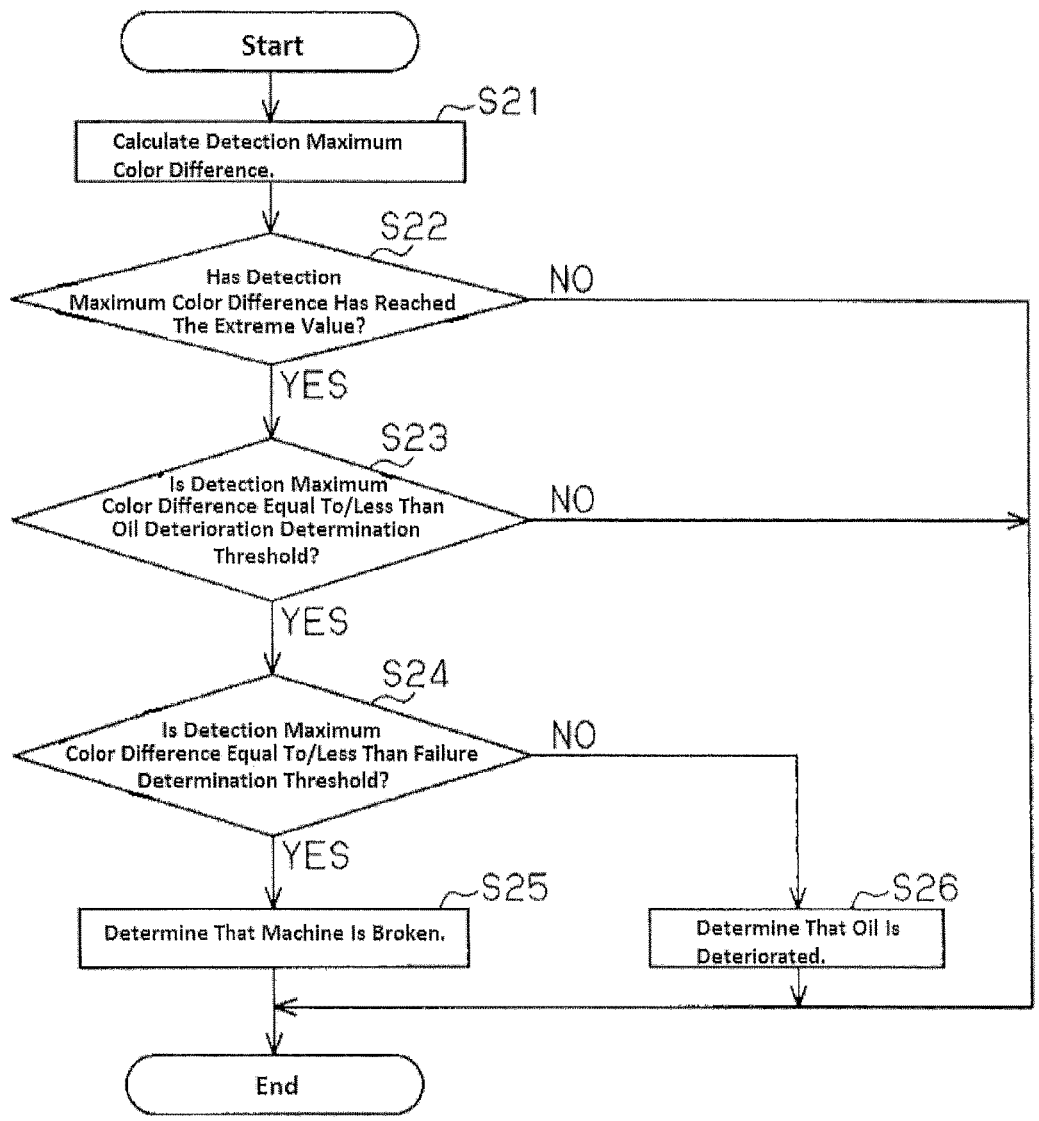
FIG. 6 is a flow chart showing a state determination method according to the second embodiment.

Referring to FIG. 6, the control unit 31 of the state determination device 30 may initiate a state determination in response to an instruction to perform the state determination. The control unit 31 calculates a detection maximum color difference from the optical sensor 20 (step S21). More specifically, the calculation unit 31*a* calculates the detection maximum color difference from a value detected by the color sensor 24 of the optical sensor 20. The calculation unit 31*a* may store the calculated detection maximum color difference in the storage unit 31*c* until the oil is replaced by a new one.

The control unit 31 may determine whether the detection maximum color difference has reached an extreme value or not (step S22). More specifically, when the maximum value of the detection maximum color differences stored in the storage unit 31*c* is determined as smaller than an extreme-value determination threshold value (step S22: NO), the determination unit 31*b* determines that the detection maximum color difference has not reached the extreme value and therefore determines that the oil is not deteriorated. The determination process is then completed.

Whereas when the maximum value of the detection maximum color differences stored in the storage unit 31*c* is determined as larger than the extreme-value determination threshold value (step S22: YES), the determination unit 31*b* determines that there is possibilities of deterioration of the oil and/or failure of the machine so that the determination process is continued.

The control unit 31 may subsequently determine whether the detection maximum color difference is less than or equal to the oil deterioration determination threshold value (step S23). More specifically, when the determination unit 31*b* determines that the detection maximum color difference calculated by the calculation unit 31*a* is larger than the oil deterioration determination threshold value (step S23: NO), the determination unit 31*b* determines that the oil is not deteriorated and the determination process is completed.

Whereas when the determination unit 31*b* determines that the detection maximum color difference calculated by the calculation unit 31*a* is less than or equal to the oil deterioration determination threshold value (step S23: YES), the determination unit 31*b* further determines whether the detection maximum color difference is less than or equal to the failure determination threshold value (step S24). More specifically, when the determination unit 31*b* determines that the detection maximum color difference is larger than the failure determination threshold value (step S24: NO), the determination unit 31*b* determines that the oil is deteriorated (step S26) and the determination process is completed. In other words, when the detection maximum color difference is larger than the failure determination threshold value and less than or equal to the oil deterioration determination threshold value, the determination unit 31*b* determines that the oil is deteriorated but the machine is not broken.

Meanwhile, when the determination unit 31*b* determines that the detection maximum color difference is smaller than or equal to the failure determination threshold value (step S24: YES), the determination unit 31*b* determines that the machine is broken (step S25) and the determination process is completed. In other words, the determination unit 31*b* determines that the oil is contaminated with impurity substances due to failure of the machine since the detection maximum color difference is less than or equal to the failure determination threshold value, and so the failure state of the machine is determined.

As described above, according to the embodiment, the maximum color difference is calculated from the value detected by the optical sensor, and it is possible to easily determine the deterioration of the oil using the oil deterioration determination threshold value and determine the failure of the machine using the failure determination threshold value.

According to the above-described embodiment, the following advantageous effects can be obtained in addition to the advantage (1) of the first embodiment. (3) When the calculated maximum color difference reaches the extreme value and is less than or equal to the oil deterioration determination threshold value, it is determined that the oil is in the deteriorated state. In case of a highly-transparent oil containing a base oil whose color tends to be easily changed due to oxidation, deterioration and the like, the maximum color difference significantly changes. Therefore when such an oil is deteriorated, the deterioration can be easily determined.

Third Embodiment

A state determination method according to a third embodiment will be now described with reference to FIGS. 7-8. The state determination method according to the third embodiment is different from the first embodiment in that a maximum color ratio is used as the calculated value instead of the brightness. The difference from the first embodiment will be mainly hereunder described. The state determination device 30 of the third embodiment may have the same structure as the state determination device 30 of the first embodiment shown in FIG. 1.

Figure 7:
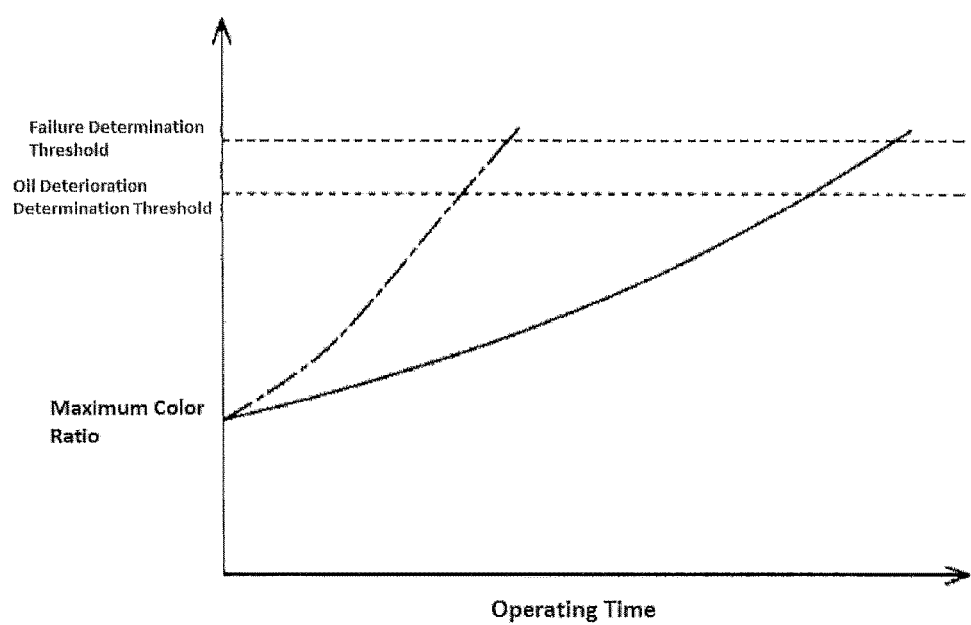
FIG. 7 illustrates a relationship between an operating time and a maximum color ratio used for determining a state according to a third embodiment.

As illustrated in FIG. 7, the maximum color ratio may increase as the operating time of the machine using oil increases. The maximum color ratio is a ratio of the maximum color component value to the minimum color component value (=the maximum color component value/the minimum color component value). The dashed-dotted line in FIG. 7 shows a change in the maximum color ratio with respect to the operating time when a load on a movable component of the machine is large. The solid line in FIG. 7 shows a change in the maximum color ratio with respect to the operating time when the load on the movable component of the machine is small. Here, the operating lime corresponds to an hour of use of the object.

The determination unit 31b may determine a deterioration state of the oil based on the maximum color ratio of the oil calculated from the detection value obtained from the optical sensor 20. More specifically, the determination unit 31b may determine the deterioration state of the oil based on comparison between the detection maximum color ratio of the oil calculated from the detection value obtained from the optical sensor 20 and the oil deterioration determination threshold value. The oil deterioration determination threshold value is a threshold value for determining whether the oil is deteriorated or not. When the detection maximum color ratio is larger than or equal to the oil deterioration determination threshold value, the determination unit 31b determines that the oil is deteriorated.

The determination unit 31b may determine a state of the machine based on the maximum color ratio of the oil calculated from the detection value obtained from the optical sensor 20. More specifically, the determination unit 31b may determine the state of the machine based on comparison between the detection maximum color ratio of the oil calculated from the detection value obtained from the optical sensor 20 and the failure determination threshold value. The failure determination threshold value is a threshold value for determining whether the machine is broken down or not and its value is larger than the oil deterioration determination threshold value. When the detection maximum color ratio is larger than or equal to the failure determination threshold value, the determination unit 31b determines that the machine is broken down. The failure state of the machine corresponds to the deterioration state.

How the state determination device 30 configured as described above determines a state will be now described with reference to FIG. 8. The state determination device 30 may periodically perform a state determination of the machine equipped with a movable component when a predetermined operating time has elapsed. Alternatively the state determination may be performed whenever a need arises or only when a user orders.

Figure 8:
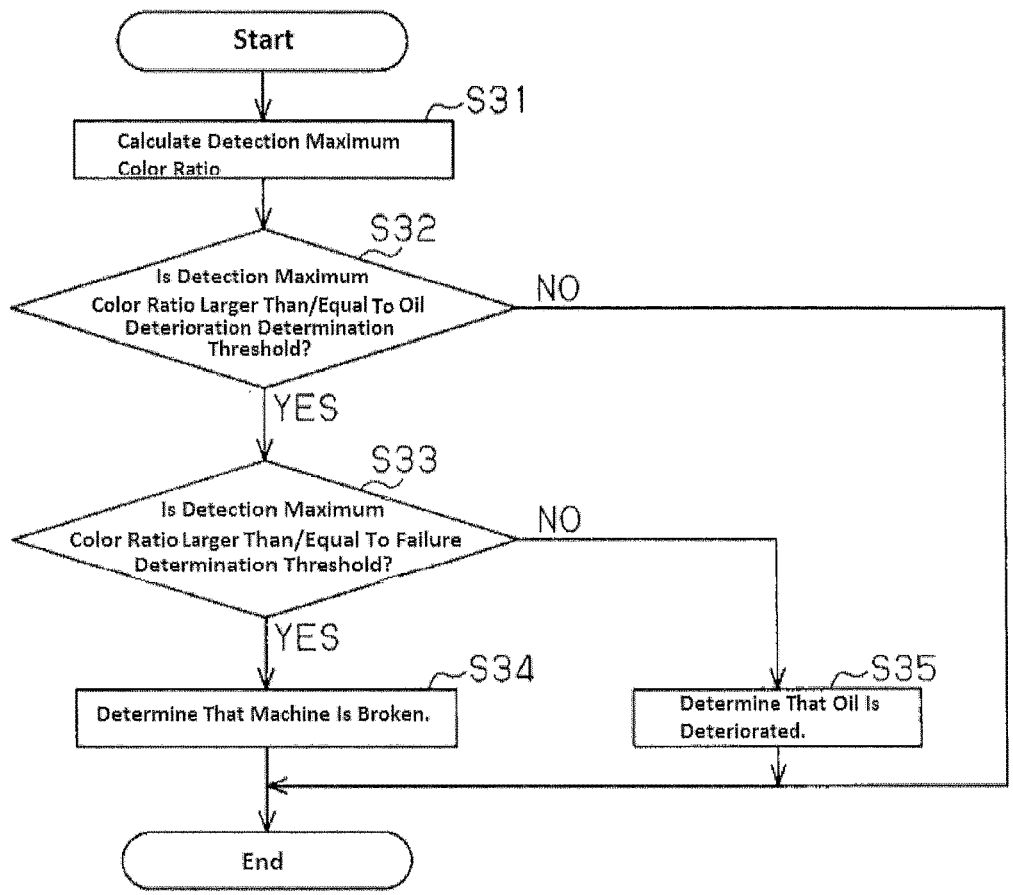
FIG. 8 is a flow chart showing a state determination method according to the third embodiment.

Referring to FIG. 8, the control unit 31 of the state determination device 30 may initiate a state determination in response to an instruction to perform the state determination. The control unit 31 calculates a detection maximum color ratio from the optical sensor 20 (step S31). More specifically, the calculation unit 31a calculates the detection maximum color ratio from a value detected by the color sensor 24 of the optical sensor 20.

The control unit 31 subsequently determines whether the detection maximum color ratio is larger than or equal to the oil deterioration determination threshold value (step S32). More specifically, when the determination unit 31b determines that the detection maximum color ratio calculated by the calculation unit 31a is less than the oil deterioration determination threshold value (step S32: NO), the determination unit 31b determines that the oil is not deteriorated and the determination process is completed.

Whereas when the determination unit 31b determines that the detection maximum color ratio calculated by the calculation unit 31a is larger than or equal to the oil deterioration determination threshold value (step S32: YES), the determination unit 31b further determines whether the detection maximum color ratio is larger than or equal to the failure determination threshold value (step S33). More specifically, when the determination unit 31b determines that the detection maximum color ratio is less than the failure determination threshold value (step S33: NO), the determination unit 31b determines that the oil is deteriorated (step S35) and the determination process is completed. In other words, when the detection maximum color ratio is larger than or equal to the oil deterioration determination threshold value and is less than or equal to the failure determination threshold value, the determination unit 31b determines that the oil is deteriorated but the machine is not broken.

Meanwhile, when the determination unit 31b determines that the detection maximum color ratio is larger than or equal to the failure determination threshold value (step S33: YES), the determination unit 31b determines that the machine is broken (step S34) and the determination process is completed. In other words, the determination unit 31b determines that the oil is contaminated with impurity substances due to failure of the machine since the detection maximum color ratio is larger than or equal to the failure determination threshold value, and so the failure state of the machine is determined.

As described above, according to the embodiment, the maximum color ratio is calculated from the value detected by the optical sensor 20, and it is possible to easily determine the deterioration of the oil using the oil deterioration determination threshold value and determine the failure of the machine using the failure determination threshold value.

According to the above-described embodiment, the following advantageous effects can be obtained in addition to the advantageous effect (1) of the first embodiment. (4) When the calculated maximum color ratio is larger than or equal to the oil deterioration determination threshold value, it is determined that the oil is in the deteriorated state. In case of a highly-transparent oil containing a base oil whose color tends to be easily changed due to oxidation, deterioration and the like, the maximum color ratio significantly changes. Therefore when such an oil is deteriorated, the deterioration can be easily determined.

Fourth Embodiment

A state determination method according to a fourth embodiment will be now described with reference to FIGS. 9-10. The state determination method according to the fourth embodiment is different from the first embodiment in that an integral of the maximum color difference is used as the calculated value instead of the brightness. The difference from the first embodiment will be mainly hereunder described. The state determination device 30 of the fourth embodiment may have the same structure as the state determination device 30 of the first embodiment shown in FIG. 1. The calculation unit 31a calculates the detection brightness and the detection maximum color difference from the value detected by the optical sensor 20, and then calculates the integral of the maximum color difference with respect to the operating time of the machine. Note that the brightness decreases as the operating time of the machine increases, whereas the maximum color ratio increases as the operating time of the machine increases and then decreases once it reaches the extreme value. The calculation unit 31a may store the calculated integrated value of the maximum color difference in the storage unit 31c until the oil is replaced by a new one. Here, the operating time corresponds to an hour of use of the object.

Figure 9:
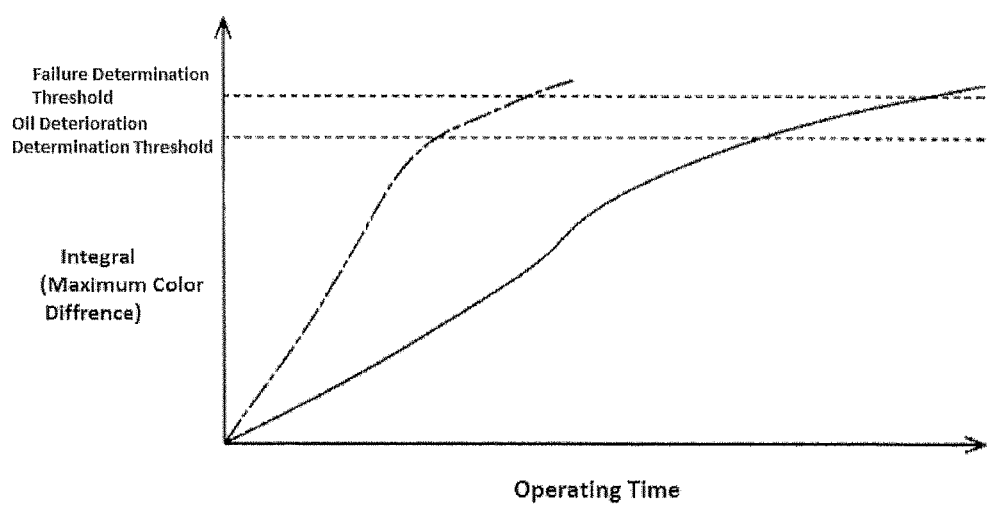
FIG. 9 illustrates a relationship between brightness and an integral of a maximum color difference used for determining a state according to a fourth embodiment.

As illustrated in FIG. 9, the integral of the maximum color difference increases as the operating time of the machine increases. The integral of the maximum color difference is an integrated value obtained by adding the maximum color difference each time the brightness changes as the operating time passes. The dashed-dotted line in FIG. 9 shows a change in the integral of the maximum color difference with respect to the brightness when a load on a movable component of the machine is large. The solid line in FIG. 9 shows a change in the integral of the maximum color difference with respect to the brightness when a load on a movable component of the machine is small.

The determination unit $31b$ may determine a deterioration state of the oil based on the integral of the maximum color difference of the oil calculated from the detection value obtained from the optical sensor 20. More specifically, the determination unit $31b$ may determine the deterioration state of the oil based on comparison between the integral of the detection maximum color difference of the oil calculated from the detection value obtained from the optical sensor 20 and the oil deterioration determination threshold value. The oil deterioration determination threshold value is a threshold value for determining whether the oil is deteriorated or not. When the integral of the detection maximum color difference is larger than or equal to the oil deterioration determination threshold value, the determination unit $31b$ determines that the oil is deteriorated.

The determination unit $31b$ may determine a state of the machine based on the integral of the maximum color difference of the oil calculated from the detection value obtained from the optical sensor 20. More specifically, the determination unit $31b$ may determine the state of the machine based on comparison between the integral of the detection maximum color difference of the oil calculated from the detection value obtained from the optical sensor 20 and the failure determination threshold value. The failure determination threshold value is a threshold value for determining whether the machine is broken down or not and its value is larger than the oil deterioration determination threshold value. When the integral of the detection maximum color ratio is larger than or equal to the failure determination threshold value, the determination unit $31b$ determines that the machine is broken down. The failure state of the machine corresponds to the deterioration state.

How the state determination device 30 configured as described above determines a state will be now described with reference to FIG. 10. The state determination device 30 may periodically perform a state determination of the machine equipped with a movable component when a predetermined operating time has elapsed. Alternatively, the determination process may performed whenever a need arises.

Figure 10:
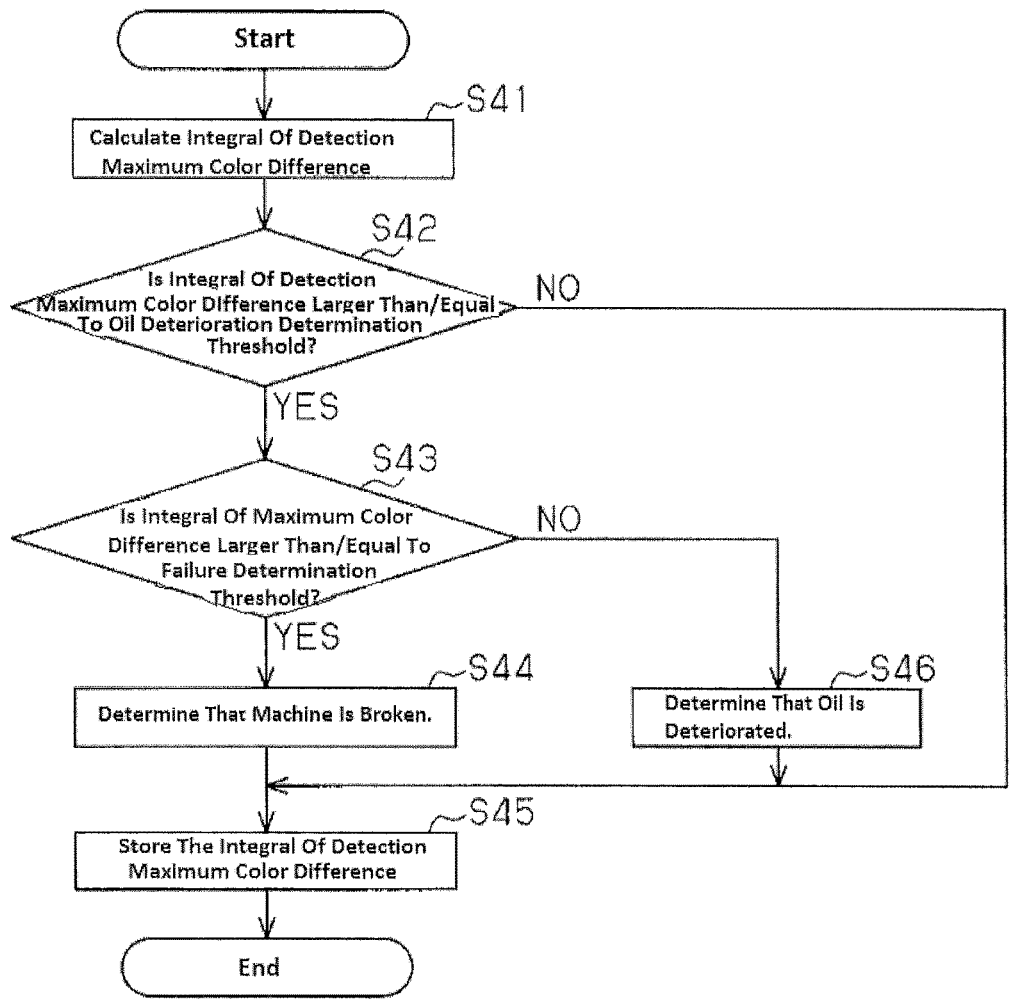
FIG. 10 is a flow chart showing a state determination method according to the fourth embodiment.

Referring to FIG. 10, the control unit 31 of the state determination device 30 may initiate a state determination in response to an instruction to perform the state determination. The control unit 31 calculates the integral of the detection maximum color difference from the optical sensor 20 (step S41). More specifically, the calculation unit $31a$ calculates the detection brightness and the detection maximum color difference from the value detected by the color sensor 24 of the optical sensor 20, and then calculates the integral of the maximum color difference with respect to the brightness. At this point, the calculation unit $31a$ obtains the integral of the maximum color difference corresponding to the past brightness from the storage unit $31c$.

The control unit 31 may subsequently determine whether the integral of the detection maximum color difference is larger than or equal to the oil deterioration determination threshold value (step S42). More specifically, when the determination unit $31b$ determines that the integral of the detection maximum color difference calculated by the calculation unit $31a$ is less than the oil deterioration determination threshold value (step S42: NO), the determination unit $31b$ determines that the oil is not deteriorated. The calculation unit $31a$ stores the calculated integral of the detection maximum color difference in the storage unit $31c$ (step S45) and then the determination process is completed.

Whereas when the determination unit $31b$ determines that the integral of the detection maximum color difference calculated by the calculation unit $31a$ is larger than or equal to the oil deterioration determination threshold value (step S42: YES), the determination unit $31b$ further determines whether the integral of the detection maximum color difference is larger than or equal to the failure determination threshold value (step S43). More specifically, when the determination unit $31b$ determines that the integral of the detection maximum color difference is less than the failure determination threshold value (step S43: NO), the determination unit $31b$ determines that the oil is deteriorated (step S46). The calculation unit $31a$ stores the calculated integral of the detection maximum color difference in the storage unit $31c$ (step S45) and then the determination process is completed. In other words, when the integral of the detection maximum color difference is larger than or equal to the oil deterioration determination threshold value and is less than or equal to the failure determination threshold value, the determination unit $31b$ determines that the oil is deteriorated but the machine is not broken.

More specifically, when the determination unit $31b$ determines that the integral of the detection maximum color difference is larger than or equal to the failure determination threshold value (step S43: YES), the determination unit $31b$ determines that the machine is broken (step S44). The calculation unit $31a$ stores the calculated integral of the detection maximum color difference in the storage unit $31c$ (step S45) and then the determination process is completed. In other words, the determination unit $31b$ determines that the oil is contaminated with impurity substances due to failure of the machine since the integral of the detection maximum color difference is less than or equal to the failure determination threshold value, and so the failure state of the machine is determined.

As described above, according to the embodiment, the integral of the maximum color difference with respect to the operating time is calculated from the value detected by the optical sensor 20, and it is possible to easily determine the deterioration of the oil using the oil deterioration determination threshold value and determine the failure of the machine using the failure determination threshold value.

According to the above-described embodiment, the following advantageous effects can be obtained in addition to the advantageous effect (1) of the first embodiment. (5) When the calculated integral of the maximum color difference is larger or equal to the oil deterioration determination threshold value, it is determined that the oil is deteriorated, and when the calculated integral of the maximum color difference is larger or equal to the failure determination threshold value, it is determined that the machine is broken. Compared with the case where the deterioration state of the oil and the machine is determined based on the relation between the brightness and the maximum color difference, in other words, the case where the two parameters, the brightness and the maximum color difference, are used to determine the deterioration state, the fourth embodiment can easily determine the state since only one parameter, that is the integral of the maximum color difference, is required.

Fifth Embodiment

A state determination method according to a fifth embodiment will be now described with reference to FIGS. 11-12. The state determination method according to the fifth embodiment is different from the first embodiment in that an integral of the maximum color ratio is used as the calculated value instead of the brightness. The difference from the first embodiment will be mainly hereunder described. The state determination device 30 of the fifth embodiment may have the same structure as the state determination device 30 of the first embodiment shown in FIG. 1. The calculation unit 31a calculates the detection brightness and the detection maximum color ratio from the value detected by the optical sensor 20, and then calculates the integral of the maximum color ratio with respect to the operating time of the machine. Note that the brightness decreases as the operating time of the machine increases, whereas the maximum color ratio increases as the operating time of the machine increases. The calculation unit 31a may store the calculated integrated value of the detection maximum color ratio in the storage unit 31c until the oil is replaced by a new one. Here, the operating time corresponds to an hour of use of the object.

Figure 11:
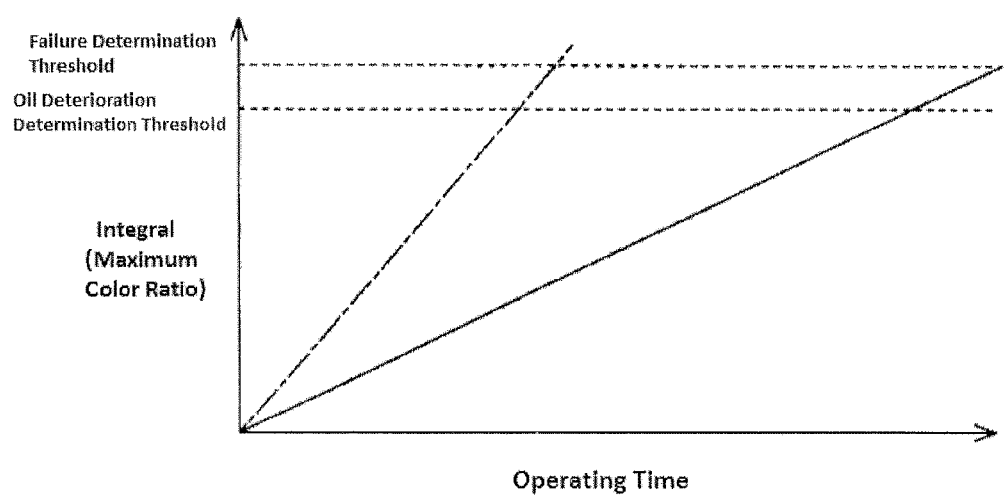
FIG. 11 illustrates a relationship between brightness and an integral of the maximum color ratio used for determining a state according to a fifth embodiment.

As illustrated in FIG. 11, the integral of the maximum color ratio may increase as the operating time of the machine increases. The integral of the maximum color ratio is an integrated value obtained by adding the maximum color ratio each time the brightness changes as the operating time passes. The dashed-dotted line in FIG. 11 shows a change in the integral of the maximum color ratio with respect to the brightness when a load on a movable component of the machine is large. The solid line in FIG. 11 shows a change in the integral of the maximum color ratio with respect to the brightness when a load on a movable component of the machine is small.

The determination unit 31b may determine a deterioration state of the oil based on the integral of the maximum color ratio of the oil calculated from the detection value obtained from the optical sensor 20. More specifically, the determination unit 31b may determine the deterioration state of the oil based on comparison between the integral of the detection maximum color ratio of the oil calculated from the detection value obtained from the optical sensor 20 and the oil deterioration determination threshold value. The oil deterioration determination threshold value is a threshold value for determining whether the oil is deteriorated or not. When the integral of the detection maximum color ratio is larger than or equal to the oil deterioration determination threshold value, the determination unit 31b determines that the oil is deteriorated.

The determination unit 31b may determine a state of the machine based on the integral of the maximum color ratio of the oil calculated from the detection value obtained from the optical sensor 20. More specifically, the determination unit 31b may determine the state of the machine based on comparison between the integral of the detection maximum color ratio of the oil calculated from the detection value obtained from the optical sensor 20 and the failure determination threshold value. The failure determination threshold value is a threshold value for determining whether the machine is broken down or not and its value is larger than the oil deterioration determination threshold value. When the integral of the detection maximum color ratio is larger than or equal to the failure determination threshold value, the determination unit 31b determines that the machine is broken down. The failure state of the machine corresponds to the deterioration state.

How the state determination device 30 configured as described above determines a state will be now described with reference to FIG. 12. The state determination device 30 may periodically perform a state determination of the machine equipped with a movable component when a predetermined operating time has elapsed. Alternatively, the determination process may performed whenever a need arises.

Figure 12:
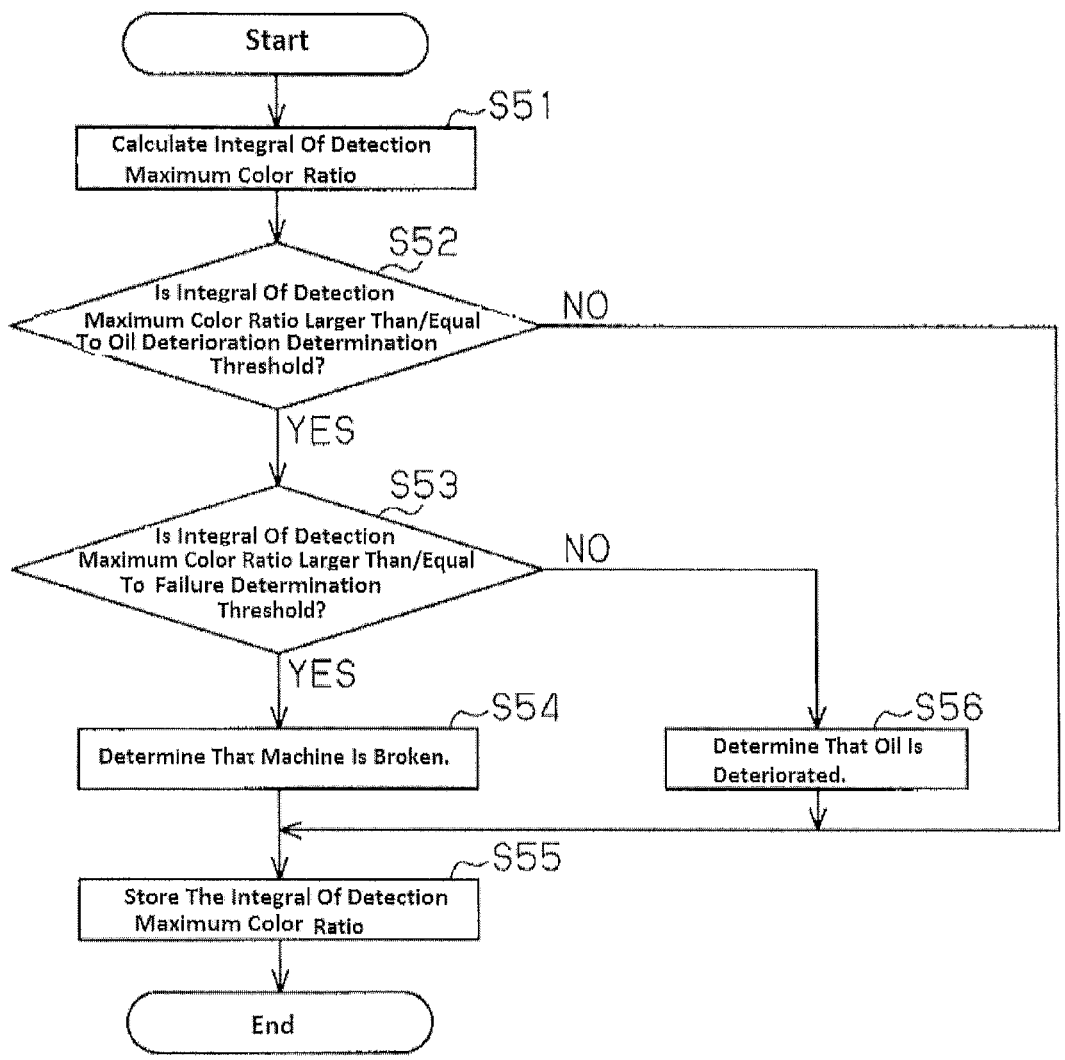
FIG. 12 is a flow chart showing a state determination method according to the fifth embodiment.

Referring to FIG. 12, the control unit 31 of the state determination device 30 may initiate a state determination in response to an instruction to perform the state determination. The control unit 31 may calculate the integral of the detection maximum color ratio from the optical sensor 20 (step S51). More specifically, the calculation unit 31a calculates the detection brightness and the detection maximum color ratio from the value detected by the color sensor 24 of the optical sensor 20, and then calculates the integral of the maximum color ratio with respect to the brightness. At this point, the calculation unit 31a obtains the integral of the maximum color ratio corresponding to the past brightness from the storage unit 31c.

The control unit 31 subsequently determines whether the integral of the detection maximum color ratio is larger than or equal to the oil deterioration determination threshold value (step S52). More specifically, when the determination unit 31b determines that the integral of the detection maximum color ratio calculated by the calculation unit 31a is less than the oil deterioration determination threshold value (step S52: NO), the determination unit 31b determines that the oil is not deteriorated. The calculation unit 31a stores the calculated integral of the detection maximum color ratio in the storage unit 31c (step S55) and then the determination process is completed.

Whereas when the determination unit 31b determines that the integral of the detection maximum color ratio calculated by the calculation unit 31a is larger than or equal to the oil deterioration determination threshold value (step S52: YES), the determination unit 31b further determines whether the integral of the detection maximum color ratio is larger than or equal to the failure determination threshold value (step S53). More specifically, when the determination unit 31b determines that the integral of the detection maximum color difference is less than the failure determination threshold value (step S53: NO), the determination unit 31b determines that the oil is deteriorated (step S56). The calculation unit 31a stores the calculated integral of the detection maximum color ratio in the storage unit 31c (step S55) and then the determination process is completed. In other words, when the integral of the detection maximum color ratio is larger than or equal to the oil deterioration determination threshold value and is less than or equal to the failure determination threshold value, the determination unit 31b determines that the oil is deteriorated but the machine is not broken.

More specifically, when the determination unit 31b determines that the integral of the detection maximum color ratio is larger than or equal to the failure determination threshold value (step S53: YES), the determination unit 31b determines that the machine is broken down (step S54). The calculation unit 31a stores the calculated integral of the detection maximum color ratio in the storage unit 31c (step S55) and then the determination process is completed. In other words, the determination unit 31b determines that the oil is contaminated with impurity substances due to failure of the machine since the integral of the detection maximum color ratio is less than or equal to the failure determination threshold value, and so the failure state of the machine is determined.

As described above, according to the embodiment, the integral of the maximum color ratio with respect to the operating time is calculated from the value detected by the optical sensor 20, and it is possible to easily determine the deterioration of the oil using the oil deterioration determination threshold value and determine the failure of the machine using the failure determination threshold value.

According to the above-described embodiment, the following advantageous effects can be obtained in addition to the advantageous effect (1) of the first embodiment. (6) When the calculated integral of the maximum color ratio is larger or equal to the oil deterioration determination threshold value, it is determined that the oil is deteriorated, and when the calculated integral of the maximum color ratio is larger or equal to the failure determination threshold value, it is determined that the machine is broken. Compared with the case where the deterioration state of the oil and the machine is determined based on the relation between the brightness and the maximum color difference, in other words, the case where the two parameters, the brightness and the maximum color difference, are required to determine the deterioration state, the fifth embodiment can easily determine the state since only one parameter, that is the integral of the maximum color ratio, is required.

The above-described embodiments can be adequately modified as described below. In the second embodiment, the detection maximum color difference is compared with the oil deterioration determination threshold value and the failure determination threshold value after the detection maximum color difference exceeds the extreme value. However, the detection maximum color difference may be compared with the oil deterioration determination threshold value and the failure determination threshold value before the maximum color difference reaches the extreme value.

In the first to fifth embodiments, the objects are oil and/or a machine, and a state of the oil is determined based on the oil deterioration determination threshold value and a state of the machine is determined based on the failure determination threshold value. However, the object may be limited to the oil, and only the state of the oil may be determined based on the oil deterioration determination threshold value. More specifically, in the first embodiment, the steps S13 and S14 may be omitted, and when the detection brightness is less than or equal to the oil deterioration determination threshold value (step S12: YES), it is determined that the oil is deteriorated (step S15). In the second embodiment, the steps S24 and S25 may be omitted, and when the detection maximum color difference reaches the extreme value (step S22: YES) and is less than or equal to the failure determination threshold value (step S23: YES), it is determined that the machine is broken out (step S26). More specifically, in the third embodiment, the steps S33 and S34 may be omitted, and when the detection maximum color ratio is larger than or equal to the oil deterioration determination threshold value (step S32: YES), it is determined that the oil is deteriorated (step S35). In the fourth embodiment, the steps S43 and S44 may be omitted, and when the integral of the detection maximum color difference is larger than or equal to the oil deterioration determination threshold value (step S42: YES), it is determined that the oil is deteriorated (step S46). In the fifth embodiment, the steps S53 and S54 may be omitted, and when the integral of the detection maximum color ratio is larger than or equal to the oil deterioration determination threshold value (step S52: YES), it is determined that the oil is deteriorated (step S56).

In the first to fifth embodiments, the objects to be judged are oil and a machine, and a state of the oil is determined based on the oil deterioration determination threshold value and a state of the machine is determined based on the failure determination threshold value. However, the object may be limited to the machine, and only the state of the machine may be determined based on the failure determination threshold value. More specifically, in the first embodiment, the steps S12 and S15 may be omitted, and when the detection brightness is less than or equal to the failure determination threshold value (step S13: YES), it is determined that the machine is broken out (step S14). In the second embodiment, the steps S23 and S26 may be omitted, and when the detection maximum color difference reaches the extreme value (step S22: YES) and is less than or equal to the failure determination threshold value (step S24: YES), it is determined that the machine is broken out (step S25). In the third embodiment, the steps S32 and S35 may be omitted, and when the detection maximum color ratio is larger than or equal to the failure deterioration determination threshold value (step S33: YES), it is determined that the machine is broken out (step S34). In the fourth embodiment, the steps S42 and S46 may be omitted, and when the integral of the detection maximum color difference is larger than or equal to the failure determination threshold value (step S43), it is determined that the machine is broken out (step S44). In the fifth embodiment, the steps S52 and S56 may be omitted, and when the integral of the detection maximum color ratio is larger than or equal to the failure determination threshold value (step S53: YES), it is determined that the machine is broken out (step S54).

In the first to fifth embodiments, the optical sensor 20 is the reflection type using a prism. However, other optical sensors such as one in which the light emitting element is disposed so as to face the light receiving element may also be used. In the first to fifth embodiments, the machine can be a machine equipped with a movable bearing, a piston and the like that requires oil. The state determination device 30 may be provided to movable components of wind generators, construction machines, aircrafts, railroad vehicles, vacuum pumps and the like. More specifically, the wind generator may include, for example, a step-up gear and its bearing for the wind generator, a pitch-driving hydraulic cylinder and a reduction gear, and a YAW driving hydraulic motor. As for the construction machine, it may include, for example, a hydraulic motor, a hydraulic cylinder, a hydraulic valve (a load sensing valve and the like), a drive motor, a rotary motor, a joint and the like. As for the aircraft, it may include, for example, a flight control actuator, a hydraulic motor and the like that drives a spoiler, an aileron, an elevator, an ladder, a flap, a slat, a brake, a steering and the like. As for the railroad vehicle, it may include, for example, an air compressor for the railroad vehicles. As for a commercial vehicle and a passenger vehicle, they may include, for example, a break actuator, a circulation pump for an engine oil, a supply pump for fuel and the like. As for a vessel, it may include, a for example, a circulation pump for an engine oil, a supply pump for fuel, a hydraulically-actuated device and equipment, and the like.

LIST OF REFERENCE NUMBERS 20 optical sensor
21 housing 21a container section
21c screw
21d first through-hole
21e second through-hole
22 circuit substrate
23 light emitting element
24 color sensor
25 first prism
25a incident surface
25b reflection surface
25c exit surface
26 second prism
27 oil entering gap
28 communication line
30 state determination device
31 control unit
31a calculation unit
31b determination unit
31c storage unit
32 operating unit
33 display unit
34 communication unit

What is claimed is:

1. A method of determining a deterioration state of an object, comprising:
determining whether a calculated value reaches a first state determination threshold value or not, the calculated value utilizing at least one of brightness and a color component value calculated from a detection value detected by an optical sensor,
wherein the optical sensor includes a gap containing liquid, an LED emitting detection light toward the gap, and a color sensor detecting color information of the detection light traveled through the liquid, and
wherein, if the calculated value reaches the first state determination threshold value,
determining whether the calculated value reaches a second state determination threshold value or not,
if the calculated value reaches the second state determination threshold value, determining that a machine using the liquid is broken, and
if the calculated value does not reach the second state determination threshold value, determining that the liquid is deteriorated.

2. The method of claim 1, wherein the deterioration state of the object is determined by utilizing a fact that the brightness, a maximum color component value, and a minimum color component value calculated from the detection value detected by the optical sensor change depending on an operating time of the object.

3. The method of claim 2, wherein the calculated value includes the brightness that decreases as the operating time increases,
wherein determining that the machine is broken comprises, when the calculated brightness is less than or equal to the second state determination threshold value, determining that the machine is broken, and
wherein determining that the liquid is deteriorated comprises, when the calculated brightness is more than the second state determination threshold value, determining that the liquid is deteriorated.

4. The method of claim 2, wherein the calculated value includes a maximum color difference between the maximum color component value and the minimum color component value, the maximum color difference increasing as the operating time increases and then decreasing upon reaching an extreme value,
wherein the method further comprises determining whether the calculated maximum color difference reaches the extreme value or not,
wherein determining that the machine is broken comprises, when the calculated maximum color difference reaches the extreme value and is less than or equal to the second state determination threshold value, determining that the machine is broken, and
wherein determining that the liquid is deteriorated comprises, when the calculated maximum color difference reaches the extreme value and is more than the second state determination threshold value, determining that the liquid is deteriorated.

5. The method of claim 2, wherein the calculated value includes a maximum color ratio of the maximum color component value to the minimum color component value, the maximum color ratio increasing as the operating time increases,
wherein determining that the machine is broken comprises, when the calculated maximum color ratio is larger than or equal to the second state determination threshold value, determining that the machine is broken, and
wherein determining that the liquid is deteriorated comprises, when the calculated maximum color ratio is less than the second state determination threshold value, determining that the liquid is deteriorated.

6. The method of claim 2, wherein the calculated value includes the brightness that decreases as the operating time increases; a maximum color difference between the maximum color component value and the minimum color component value, the maximum color difference increasing as the operating time increases and then decreasing upon reaching an extreme value; and an integral of the maximum color difference,
wherein determining that the machine is broken comprises, when the calculated integral of the maximum color difference is larger than or equal to the second state determination threshold value, determining that the machine is broken, and
wherein determining that the liquid is deteriorated comprises, when the calculated integral of the maximum color difference is less than the second state determination threshold value, determining that the liquid is deteriorated.

7. The method of claim 2, wherein the calculated value includes the brightness that decreases as the operating time increases; a maximum color ratio of the maximum color component value to the minimum color component value, the maximum color ratio increasing as the operating time increases; and an integral of the maximum color ratio,
wherein determining that the machine is broken comprises, when the calculated integral of the maximum color ratio is larger than or equal to the second state determination threshold value, determining that the machine is broken, and
wherein determining that the liquid is deteriorated comprises, when the calculated integral of the maximum color ratio is less than the second state determination threshold value, determining that the liquid is deteriorated.

8. A state determination device, comprising
a controller communicated with an optical sensor including a gap containing liquid, an LED emitting detection light toward the gap and a color sensor for detecting color information of the detection light traveled through the liquid;

wherein the controller is configured for
determining whether a calculated value reaches a first state determination threshold value or not, the calculated value utilizing at least one of brightness and a color component value calculated from a detection value detected by the optical sensor, wherein, if the calculated value reaches the first state determination threshold value, determining whether the calculated value reaches a second state determination threshold value or not, if the calculated value reaches the second state determination threshold value, determining that a machine using the liquid is broken, and if the calculated value does not reach the second state determination threshold value, determining that the liquid is deteriorated.

* * * * *